(12) United States Patent
Kim et al.

(10) Patent No.: US 8,882,824 B2
(45) Date of Patent: Nov. 11, 2014

(54) EXPANDING VASCULAR STENT

(75) Inventors: Sang-Ho Kim, Seongnam-Si (KR);
Jong-Chae Park, Osan-si (KR);
Eun-Jin Kim, Seongnam-si (KR);
Il-Gyun Shin, Anyang-si (KR);
Dong-Gon Kim, Yeosu-si (KR); Han-Ki Kim, Anyang-si (KR)

(73) Assignee: CG Bio Co., Ltd., Gyeonggi-do (KR)

( * ) Notice: Subject to any disclaimer, the term of this patent is extended or adjusted under 35 U.S.C. 154(b) by 0 days.

(21) Appl. No.: 12/922,676

(22) PCT Filed: Apr. 20, 2010

(86) PCT No.: PCT/KR2010/002469
§ 371 (c)(1),
(2), (4) Date: Apr. 13, 2011

(87) PCT Pub. No.: WO2011/132803
PCT Pub. Date: Oct. 27, 2011

(65) Prior Publication Data
US 2011/0257727 A1   Oct. 20, 2011

(51) Int. Cl.
*A61F 2/06* (2013.01)
*A61F 2/915* (2013.01)

(52) U.S. Cl.
CPC ....... *A61F 2/915* (2013.01); *A61F 2002/91575* (2013.01); *A61F 2002/91525* (2013.01)
USPC .................................. 623/1.15

(58) Field of Classification Search
CPC .................. A61F 2/915; A61F 2002/91525
USPC ................ 623/1.15–1.16, 1.12, 1.18–1.21
See application file for complete search history.

(56) References Cited

U.S. PATENT DOCUMENTS

| | | | | |
|---|---|---|---|---|
| 5,911,754 A | * | 6/1999 | Kanesaka et al. | 623/1.15 |
| 5,935,162 A | * | 8/1999 | Dang | 623/1.15 |
| 6,039,756 A | * | 3/2000 | Jang | 623/1.15 |
| 6,042,597 A | * | 3/2000 | Kveen et al. | 623/1.15 |
| 6,053,940 A | * | 4/2000 | Wijay | 623/1.15 |
| 6,083,259 A | * | 7/2000 | Frantzen | 623/1.15 |
| 6,123,721 A | * | 9/2000 | Jang | 623/1.15 |
| 6,179,867 B1 | * | 1/2001 | Cox | 623/1.15 |
| 6,187,034 B1 | * | 2/2001 | Frantzen | 623/1.11 |
| 6,193,747 B1 | * | 2/2001 | von Oepen | 623/1.15 |
| 6,200,334 B1 | * | 3/2001 | Jang | 623/1.15 |
| 6,235,053 B1 | * | 5/2001 | Jang | 623/1.15 |
| 6,261,319 B1 | * | 7/2001 | Kveen et al. | 623/1.15 |
| 6,331,189 B1 | * | 12/2001 | Wolinsky et al. | 623/1.15 |
| 6,428,570 B1 | * | 8/2002 | Globerman | 623/1.15 |
| 6,461,380 B1 | * | 10/2002 | Cox | 623/1.17 |
| 6,464,722 B2 | * | 10/2002 | Israel et al. | 623/1.17 |
| 6,478,816 B1 | * | 11/2002 | Kveen et al. | 623/1.15 |

(Continued)

*Primary Examiner* — Alvin Stewart
(74) *Attorney, Agent, or Firm* — Intellectual Property Law Group LLP

(57) ABSTRACT

An expanding vascular stent is disclosed that is inserted into a blood vessel in the human body and expands the blood vessel. The stent is configured in such a way that adjacent rows, each of which is comprised of a plurality of identical cells, are symmetrically arranged, in an out of phase manner. When the stent is expanded in the radial direction, the adjacent rows are expanded in opposite directions, maintaining their linearly symmetrical state. Therefore, the reduction in the length of the stent can be minimized. Since the stent has also a great degree of flexibility, when it is inserted into the blood vessel, it can minimize the damage to the blood vessel wall.

5 Claims, 6 Drawing Sheets

(56) References Cited

U.S. PATENT DOCUMENTS

| | | | |
|---|---|---|---|
| 6,613,079 B1 * | 9/2003 | Wolinsky et al. | 623/1.15 |
| 6,616,689 B1 * | 9/2003 | Ainsworth et al. | 623/1.16 |
| 6,626,935 B1 * | 9/2003 | Ainsworth et al. | 623/1.15 |
| 6,629,994 B2 * | 10/2003 | Gomez et al. | 623/1.15 |
| 6,635,083 B1 * | 10/2003 | Cheng et al. | 623/1.15 |
| 6,638,300 B1 * | 10/2003 | Frantzen | 623/1.15 |
| 6,652,579 B1 * | 11/2003 | Cox et al. | 623/1.34 |
| 6,679,911 B2 * | 1/2004 | Burgermeister | 623/1.17 |
| 6,749,629 B1 * | 6/2004 | Hong et al. | 623/1.15 |
| 6,764,507 B2 * | 7/2004 | Shanley et al. | 623/1.16 |
| 6,776,793 B2 * | 8/2004 | Brown et al. | 623/1.15 |
| 6,878,162 B2 * | 4/2005 | Bales et al. | 623/1.15 |
| 6,945,993 B2 * | 9/2005 | Kveen et al. | 623/1.15 |
| 6,962,603 B1 * | 11/2005 | Brown et al. | 623/1.15 |
| D523,558 S * | 6/2006 | Shanley | D24/155 |
| 7,179,285 B2 * | 2/2007 | Ikeuchi et al. | 623/1.15 |
| 7,204,848 B1 * | 4/2007 | Brown et al. | 623/1.15 |
| 7,247,166 B2 * | 7/2007 | Pienknagura | 623/1.15 |
| 7,316,710 B1 * | 1/2008 | Cheng et al. | 623/1.15 |
| 7,404,823 B2 * | 7/2008 | Gregorich et al. | 623/1.15 |
| 7,465,315 B2 * | 12/2008 | Morris et al. | 623/1.15 |
| 7,534,258 B2 * | 5/2009 | Gomez et al. | 623/1.17 |
| 7,594,927 B2 * | 9/2009 | Majercak et al. | 623/1.15 |
| 7,611,531 B2 * | 11/2009 | Calisse | 623/1.15 |
| 7,722,658 B2 * | 5/2010 | Richter et al. | 623/1.15 |
| 7,789,905 B2 * | 9/2010 | Von Oepen et al. | 623/1.15 |
| 7,815,672 B2 * | 10/2010 | Von Oepen et al. | 623/1.15 |
| 7,842,078 B2 * | 11/2010 | Von Oepen et al. | 623/1.15 |
| 7,846,196 B2 * | 12/2010 | Von Oepen et al. | 623/1.15 |
| 7,862,606 B2 * | 1/2011 | Lootz et al. | 623/1.16 |
| 7,887,577 B2 * | 2/2011 | Von Oepen et al. | 623/1.15 |
| 7,927,364 B2 * | 4/2011 | Fierens et al. | 623/1.15 |
| 7,959,999 B2 * | 6/2011 | Prabhu | 428/36.9 |
| 7,967,852 B2 * | 6/2011 | Addonizio et al. | 623/1.15 |
| 7,985,251 B2 * | 7/2011 | Ikeuchi et al. | 623/1.15 |
| 8,016,876 B2 * | 9/2011 | Gregorich et al. | 623/1.15 |
| 8,025,916 B2 * | 9/2011 | Hossainy et al. | 427/2.24 |
| 8,029,558 B2 * | 10/2011 | Ta et al. | 623/1.35 |
| 8,038,705 B2 * | 10/2011 | Brown et al. | 623/1.15 |
| 8,043,358 B2 * | 10/2011 | Weber et al. | 623/1.15 |
| 8,048,142 B2 * | 11/2011 | Venturelli | 623/1.15 |
| 8,057,530 B2 * | 11/2011 | Kusleika et al. | 623/1.15 |
| 8,070,792 B2 * | 12/2011 | Gregorich et al. | 623/1.15 |
| 8,092,514 B1 * | 1/2012 | Khosravi et al. | 623/1.15 |
| 8,114,149 B2 * | 2/2012 | Fischell et al. | 623/1.15 |
| 8,157,855 B2 * | 4/2012 | Eidenschink et al. | 623/1.15 |
| 8,211,161 B2 * | 7/2012 | Limon | 623/1.15 |
| 8,328,864 B2 * | 12/2012 | Niermann | 623/1.16 |
| 8,348,991 B2 * | 1/2013 | Weber et al. | 623/1.15 |
| 8,449,597 B2 * | 5/2013 | Brown | 623/1.15 |

* cited by examiner (a)

(b)

(a)

(b)

EXPANDING VASCULAR STENT

BACKGROUND OF THE INVENTION

1. Field of the Invention

The present invention relates to medical devices, and more particularly to an expanding vascular stent that is inserted into a blood vessel in the human body and expands the blood vessel, where it is improved in terms of structure to enhance its performance, compared with conventional stents.

2. Background of the Invention

A stent is an artificial tube inserted into a conduit in the human body, such as a blood vessel, etc., to hold the conduit open. The stent is shaped as a cylindrical hollow. The stent is inserted into a blood vessel, etc., opens a strangulated portion and holds it open.

First, the stent needs a high expansion force to hold its cylindrical hollow shape. Second, it is preferable that the stent is as small as possible in the lengthwise and radial directions when it is initially expanded in the radial direction. Third, the stent requires a large degree of flexibility so that it does not damage the blood vessel wall or a balloon catheter when being inserted into a zigzagged blood vessel.

In order to faithfully follow the conditions described above, research and development have been performed using conventional stents. According to US FDA guidelines, when a stent is initially expanded in the radial direction, the change in the length and radius of the stent is restricted to 5~7%. In particular, they treat the expansion of the stent in the radial direction as an important factor.

A great deal of research has been conducted on conventional stents conforming to the conditions described above, which were disclosed in Korean Patent Publication No. 10-2004-0075346, U.S. Pat. Nos. 7,326,241 and 7,442,203. For example, they have disclosed stents having the same cells being regularly repeated.

SUMMARY OF THE INVENTION

The present invention solves the above problems, and provides an expanding vascular stent that is minimized in length and radial directions when it is inserted into a blood vessel in the body and initially expands in the radial direction, but that has a high degree of flexibility in the radial direction, thereby minimizing the damage to the blood vessel.

In accordance with an exemplary embodiment of the present invention, there is provided an expanding vascular stent including: a body that is hollow in the lengthwise direction. The body includes a plurality of rows connected to each other, each row including a plurality of cells joined together. The adjacent rows are located in such a way that the plurality of cells in one row are symmetrically formed to the plurality of cells in another row, in an out of phase array.

In accordance with another exemplary embodiment of the present invention, there is provided an expanding vascular stent including a body that is hollow in the lengthwise direction, including a plurality of cells joined together. Each of the plurality of cells includes at least two or more parts whose body is curved numerous times and whose one side is opened, in which both ends of the part are extended with a curved portion, the curved portions being curved in the same direction.

Preferably, each of the plurality of cells includes first, second and third parts. The first part has a plurality of curved portions. The first part is symmetrically formed and opens on one side. The a second part has a plurality of curved portions, wherein the second part is joined to the first part, one end of the second part is symmetrically formed to the other end of the second part, and the second part is open on one side. The third part is symmetrically formed to the first part. The third part is joined to the second part.

Preferably, the first cell includes a first unit having at least four curved portions and a second unit having at least two curved portions, where the second unit is joined to the first unit.

Preferably, the second cell includes a unit having at least four curved portions, located at its one side, and another unit at the other side, in which the unit is symmetrically joined to another unit.

Preferably, the body includes a plurality of rows each of which is comprised of a plurality of cells joined together. The plurality of rows are symmetrical with respect to the lengthwise direction of the rows and out of phase to each other.

Preferably, the body includes first and second rows each of which is comprised of the plurality of cells joined together, and links each of which connects a first part of the first row to a third part of the second row.

Preferably, each of the first and third parts includes: a first unit having at least four curved portions; and a second unit having at least two curved portions, the second unit being joined to the first unit. The link connects the first unit of the first part in the first row to the first unit of the third part in the second row.

Preferably, the body includes: a first row comprised of a plurality of cells joined together; a second row comprised of a plurality of cells joined together; and a link connecting the second part in the first row to the second part in the second row.

Preferably, the second part includes: a first unit having at least four curved portions, located at one side of the second part; and a second unit that is located at the other side of the second part and symmetrically joined to the first unit. The link connects the second unit of the second part in the first row to the first unit of the second part in the second row.

Preferably, the body includes: a first row having a plurality of cells joined together; a second row having a plurality of cells joined together; a third row having a plurality of cells joined together; a first link connecting the first part in the first row to the third part in the second row; and a second link connecting the second part in the first row to the second part in the second row. The first and the second links are out of phase.

In accordance with another exemplary embodiment of the present invention, there is provided an expanding vascular stent including: a body that is hollow in the lengthwise direction, having a plurality of cells joined together. Each of the plurality of cells includes: a plurality of first units each of which has at least four curved portions; and a plurality of second units each of which has at least two curved portions. Two first units and one second unit are located on one side and they are symmetrical to the units on the other side.

Preferably, the plurality cells are joined together in order as the first unit, second unit, and first unit, with respect to a virtual axis.

As described above, the stent is configured in such a way that adjacent rows, each of which is comprised of a plurality of identical cells, are symmetrically located in relation to each other, with being out of phase. Although the stent is expanded in the radial direction, the adjacent rows are expanded in the opposite directions, maintaining their linearly symmetrical state, thereby minimizing any reduction in the length of the stent.

In addition, since the stent is configured in such a way that adjacent rows, each of which is comprised of a plurality of identical cells, are symmetrically located to each other, with being out of phase, it has a high degree of flexibility. The flexibility indicates the degree to which the stent is curved when an external force is applied to one side of the stent where the other side of the stent is fixed. When a stent with a high degree of flexibility is inserted into a zigzagged blood vessel, it can minimize damage to the blood vessel wall in the human body.

Also, since the cells of the stent are symmetrically formed, when the stent is expanded in the radial direction, the plurality of parts composing the cells are symmetrically formed. Therefore, one cell can be uniformly expanded in both directions.

Furthermore, since one cell of the stent is comprised of at least two or more parts and each of the parts forms a plurality of convex and concave portions in the same directions, correspondingly and respectively, when the stent is compressed in the radial direction and inserted into the human body, the convex and concave portions are compressed in the same directions correspondingly and respectively. Therefore, the stent can be compressed to the highest degree possible.

BRIEF DESCRIPTION OF THE DRAWINGS

The features and advantages of the present invention will become more apparent from the following detailed description in conjunction with the accompanying drawings, in which FIGS. 1A and 2B illustrate an expanding vascular stent according to an embodiment of the present invention;

FIGS. 2A and 2B illustrate one of the plurality of cells that compose an expanding vascular stent according to an embodiment of the present invention;

BRIEF DESCRIPTION OF SYMBOLS IN THE DRAWINGS

100: stent
110*a*: first cell
110*b*: second cell
110*c*: third cell
112*a*: first part
112*b*: second part
112*c*: third part
p: first unit
q: second unit
r: third unit
s: fourth unit
120*a*: first link
120*b*: second link
I: row first
II: second row
III: third row
X: virtual axis

DETAILED DESCRIPTION OF THE INVENTION

Hereinafter, exemplary embodiments of the present invention are described in detail with reference to the accompanying drawings. Detailed descriptions of well-known functions and structures incorporated herein may be omitted to avoid obscuring the subject matter of the present invention.

Figure 1:
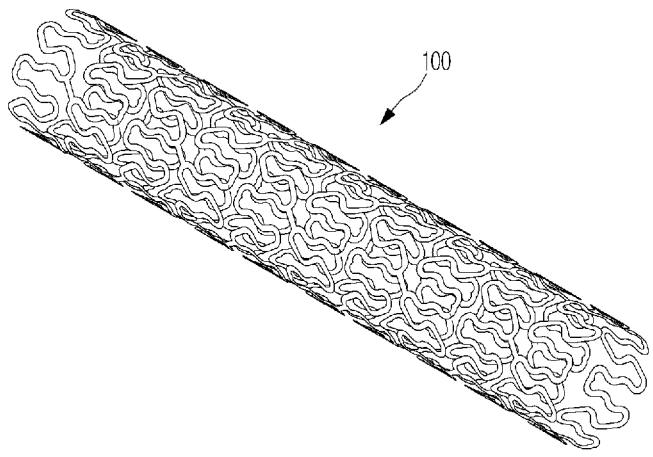
Figure 1:
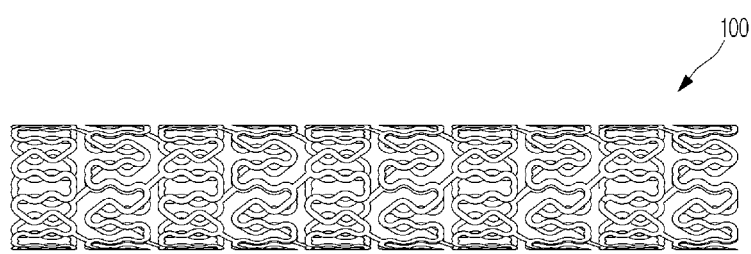
Figure 2:
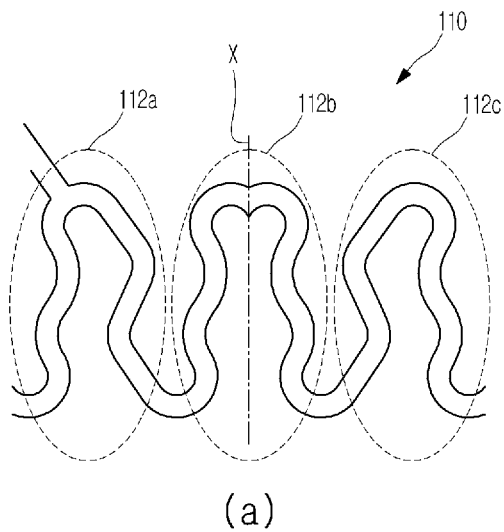
Figure 2:
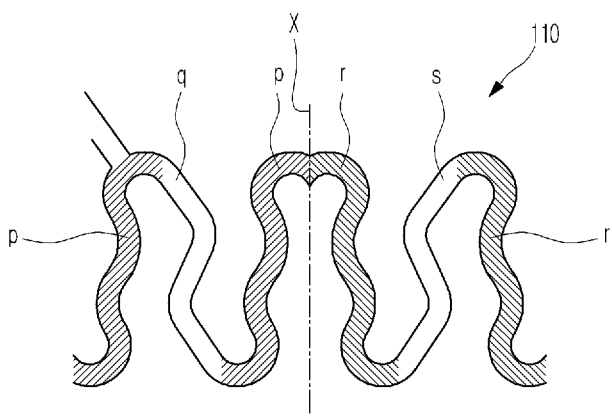

Referring to FIGS. 1A and 1B, the stent according to an embodiment of the present invention is shaped as a cylindrical hollow body that is comprised of a plurality of cells 110 joined together. The stent 100 is explained in detail with reference to FIGS. 1A to 5 as follows.

The stent 100 is structured in such a way that closed curve shapes are repeatedly joined together, forming its body. The repeatedly identical shape is called a cell 110. A cell composing the stent 100 may be shaped differently according to the definition. In the following embodiment of the present invention, however, it is assumed that the cell 110 is shaped as shown in FIGS. 2A and 2B. The cell 110 is configured to include first part 112*a*, second part 112*b*, and third part 112*c*.

As shown in FIG. 2A, the first part 112*a* is shaped as the letter 'C'. It is configured by a plurality of curves, is asymmetrical, and opens on one side. In more detail, the first part 112*a* is formed by the first unit p having four curved portions and the second unit q having two curved portions, where the first unit p is joined to the second unit q at each end of one side, so that the ends of the other side are opened.

As shown in FIG. 2B, the first unit p has four curved portions. Both opposite curved portions of the first unit p are curved facing opposite directions, so that they can be joined to the second unit q or an adjacent first unit symmetrically located to the first unit p. The four curved portions of the first unit p allow the first unit p to form two convex portions and two concave portions.

In addition, both opposite curved portions of the first unit p are more curved compared with the two remaining curved portions in the middle of the first unit p, so that the four curved portions approximately form the letter 'C'.

As shown in FIG. 2B, the second unit q of the first part 112*a* is located between the first unit p of the first part 112*a* and a first unit p of the second part 112*b*. That is, the free end of the second unit q of the first part 112*a* is joined to one side end of the first unit p of the second part 112*b*. The second unit q of the first part 112*a* has two curved portions. That is, the two curved portions of the second unit q allow the second unit q to form one convex portion and one concave portion.

The free end of the second unit q is curved so that it can be smoothly connected to the first unit p of the second unit 112*b*. The second unit q is formed in such a way that its convex and concave portions have a curvature that is smaller than the convex and concave portions of the first unit p, and the other portions (which do not include the convex and concave portions) are formed to be straight.

That is, the second unit q is shaped to be angled by the straight portions, i.e., as a sigmoidal link, compared with the shape of the first unit p.

The shape of the curved portion of the first unit p needs to be formed in the same direction as the shape of the curved portion of the second unit q. This is because, when the stent 100 is compressed in the radial direction, the curved portions of the first and second units p and q need to be close to each other without overlapping. In that case, the stent 100 can be maximally compressed in the radial direction.

When the stent 100 is compressed in the radial direction, the entire shape of the first part 112*a* leans to the left, with respect to FIG. 2B. This is because it is shown that the overall shape of the first unit p is shaped approximately as a straight line and the shape of the second unit q leans to the lower right.

As shown in FIG. 2A, the second part 112b is symmetrically formed with respect to the virtual axis X. That is, the second part 112b is formed in such a way that the first unit p is joined to a third unit r that is symmetrically formed as the first unit p with respect to the virtual axis X. Only the portion joining the first unit p and the third unit r is not smooth in the cell 110, i.e., sharply bent.

That is, this sharply bent portion is formed because both end portions of the first unit p and the third unit r are curved as an approximately semi-circle and they are symmetrically connected to each other with respect to the virtual axis X, as shown in FIGS. 2A and 2B.

As shown in FIG. 2A, the third part 112c is symmetrically formed as the first part 112a, with respect to the virtual axis X. That is, the first unit p is configured in such a way that a third unit r, symmetrically formed as the first unit p of the first part 112a with respect to the virtual axis X, is joined to a fourth s that is formed as the second unit q of the first part 112a with respect to the virtual axis X.

Therefore, the first part 112a, second part 112b, and third part 112c are joined together to form the cell 110 that is symmetrical with respect to the virtual axis X.

Referring to FIGS. 2A and 2B, the cell 110 is formed in such a way that one line is curved a number of times and has elasticity, so that it is expandable in both widthwise directions under an external force but is restored when the external force is removed.

As described above, since the first to third parts 112a~112c have corresponding units p, q, r and s, and the units p, q, r, and s are curved many times, respectively, the stent 100 can be made of a high density material. Therefore, the stent 100 is advantageous in that it can be effectively expanded in the radial direction.

Figure 3:
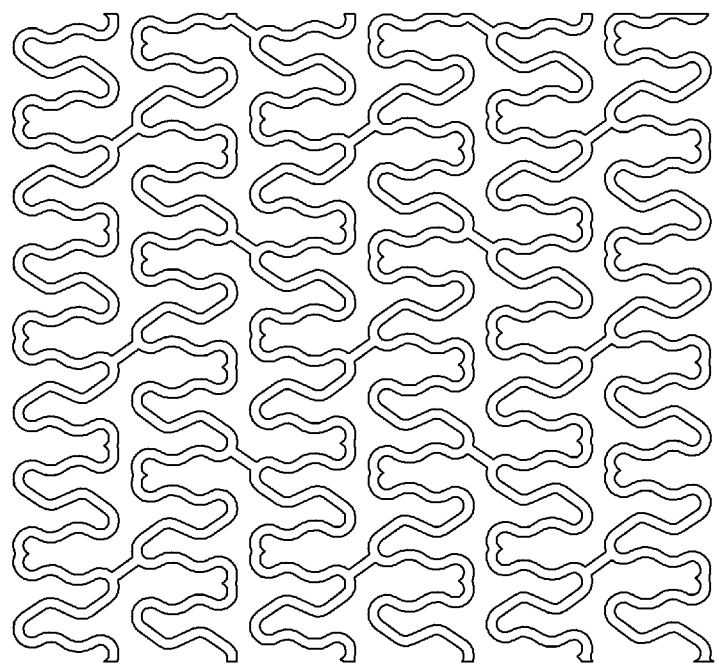
FIG. 3 is a detailed view illustrating the plurality of cells that compose an expanding vascular stent according to an embodiment of the present invention.

When the cell 110 described above is plurally joined together, theses calls form a structure, i.e., a rolled out stent 100, as shown in FIG. 3. One cell 110 is joined to another sequentially forming a row and then the row is joined to the other rows sequentially, thereby forming the rolled out stent 100.

Figure 4:
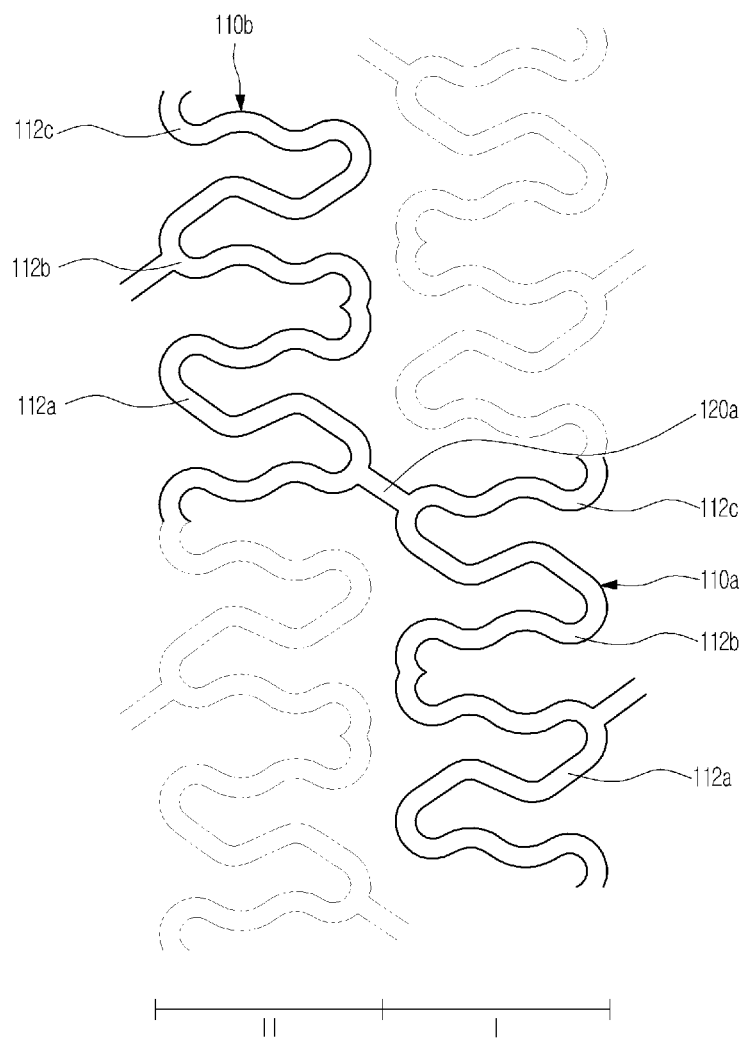
FIG. 4 is a detailed view illustrating two rows joined together, composing an expanding vascular stent according to an embodiment of the present invention.
Figure 5:
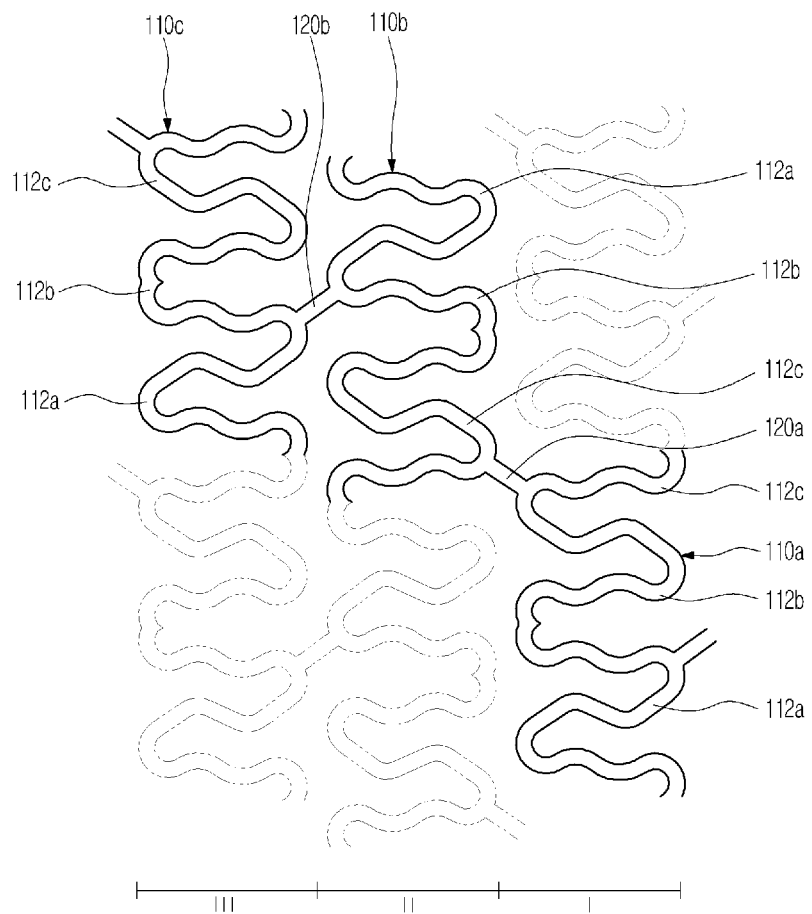
FIG. 5 is a detailed view illustrating three rows joined together, composing an expanding vascular stent according to an embodiment of the present invention.

In more detail, as shown in FIGS. 4 and 5, a first row I and a second row II, each formed by joining the cells, are connected to each other according to a certain rule. That is, the adjacent first row I and second row II are arranged as their virtual axes are out of phase, as shown in FIG. 3.

For the sake of convenience, as shown in FIG. 4, it is assumed that a cell in the first row I is called a first cell 110a and a cell in the second row II is called a second cell 110b. The first cell 110a and second cell 110b are located symmetrically and out of phase and a third part 112c of the first cell 110a is joined to a third part 112c of the second cell 110b via a first link 120a, so that the first row I is connected to the second row II.

As shown in FIG. 4, the first link 120a joins the first cell 110a and the second cell 110b so that the straight portion of the fourth unit s of the third part 112c of the first cell 110a is parallel to that of the fourth unit s of the third part 112a of the second cell 110b. Therefore, the configured shape of the first cell 110a of the first row I is symmetrical to that of the second cell 110b of second row II. If the stent 100 is expanded in the radial direction, the lengths of the first and second rows I and II are decreased in opposite directions, so that the change in the entire length of the first and second rows I and II can be reduced.

As shown in FIG. 5, three rows, for example, first, second and third rows I, II and III are joined together. The first cell 110a of the first row I is the same shape as the third cell 110c of the third row III. The second cell 110b of the second row II is linearly symmetrical to them. The first cell 110a of the first row I is parallel to the third cell 110c of the third row III in phase.

The first link 120a connecting the first row I and the second row II is opposite, in direction, to the second link 120b connecting the second row II and the third row III, with the links being out of phase.

The arrangement where the first link 120a and the second link 120b face the opposite directions, thus being out of phase, is designed so that the first and second links 120a and 120b are parallel to the directions of the straight portions of the second units q, respectively. Therefore, via the second link 120b, the portion joining the first part 112a and the second part 112b of the second cell 110b in the second row II is connected to the portion joining the first part 112a and the second part 112b of the third cell 110b in the third row III. In an embodiment of the present invention, although the first and second links 120a and 120b are formed to be straight, it should be understood that the present invention is not limited to the embodiment. For example, the first and second links 120a and 120b may have a plurality of curved portions.

Via the second link 120b, the first unit p of the second part 112b at a portion joining the first part 112a and the second part 112b is connected to the first unit p of the second part 112b at a portion joining the first part 112a and the second part 112b. The second link 120b is parallel to the straight portions of the second unit q of the first part 112a of the first cell 110a and the second unit q of the first part 112a of the second cell 110b.

As shown in FIG. 5, the first and second links 120a and 120b connect the first, second, and third rows I, II, and III. Therefore, if the stent 100 is expanded in the radial direction, the change in its length can be minimized in the lengthwise direction.

When the stent 100 is expanded in the radial direction, the change in length can be acquired via a measurement know as Foreshortening, expressed as the following equation (1). Foreshortening refers to an index to indicate a ratio of changes in the length according to pressure applied to an object in order to expand it in the radial direction.

$$\text{Foreshortening} = \frac{L_{original} - L_{load}}{L_{original}} (\%) \qquad (1)$$

Where $L_{original}$ denotes the initial length of the stent 100 and $L_{load}$ denotes a length when the stent 100 is load expanded in the radial direction. In an embodiment of the present invention, Foreshortening is calculated as 2~3%.

The relationship between the change in the length and the radius of the stent 100 when the stent 100 is expanded in the radial direction at the initial state and the change of the length and the radius of the stent 100 when the expanded stent 100 is reduced can be checked by a measurement known as Recoil. Recoil is distinguished between Longitudinal Recoil indicating the change in the length in the length direction of the stent 100 and Radial Recoil indicating the change in the radius in the radial direction, which are expressed as following equations (2) and (3), respectively.

$$\text{Logitudinal Recoil} = \frac{L_{load} - L_{unload}}{L_{load}} \times 100\% \qquad (2)$$

Where $L_{load}$ denotes a length when the stent 100 is expanded in the radial direction and $L_{unload}$ denotes a length when it is shrunk.

$$\text{Radial Recoil} = \frac{D_{load} - D_{unload}}{D_{load}} \times 100\% \qquad (3)$$

Where $D_{load}$ denotes a radius when the stent 100 is expanded in the radial direction and $D_{unload}$ denotes a radius when it is reduced. In an embodiment of the present invention, Redial Recoil is calculated as 13~16%.

Figure 6:
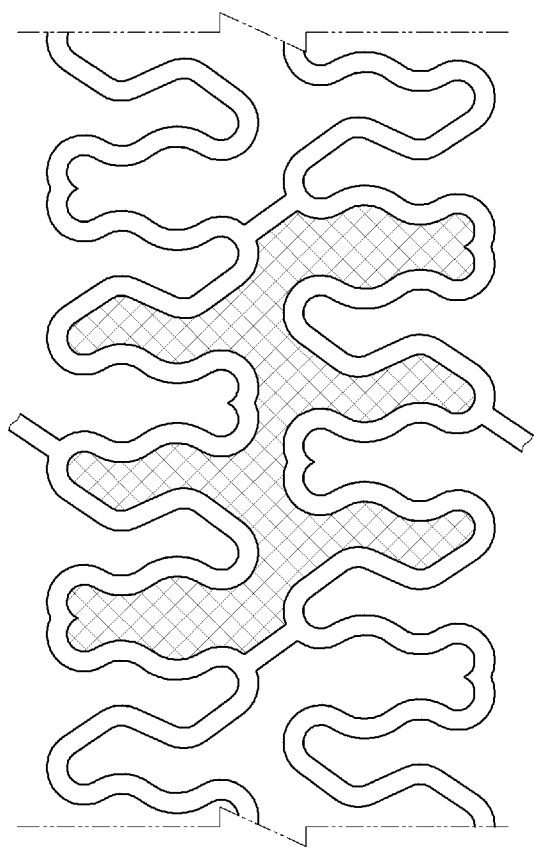
FIG. 6 is a view illustrating a cell showing side branch access and a closed curve of the cell, composing an expanding vascular stent according to an embodiment of the present invention.

As shown in FIG. 6, Side Branch Access measures how far a new stent can be inserted into a blood vessel where another stent has already been inserted into another blood vessel adjacent to the blood vessel by comparing the entire area of a closed curve formed by a primary cell and connected cells or the length thereof between the two stents. Therefore, the larger the entire area of the length of the closed curve, the easier it is for the stent 100 to be inserted into the blood vessel.

It is preferable that the stent 100 is made of material harmless to the human body, for example, Co—Cr alloy group, stainless material, Nitinol, etc.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An expanding vascular stent comprising:
    a body that is hollow in the lengthwise direction, including a plurality of cells joined together,
    wherein each of the plurality of cells includes at least two or more parts whose body is curved numerous times and whose one side is opened, in which both ends of the parts are extended with a curved portion, the curved portions being curved in the same direction; and
    wherein each of the plurality of cells comprises:
        a first part having a plurality of curved portions, the first part being symmetrically formed with respect to a virtual axis that extends along the lengthwise direction of the stent, and open on one side;
        a second part having a plurality of curved portions, wherein the second part is joined to the first part, one end of the second part is symmetrically formed to the other end of the second part with respect to the virtual axis located through a center of the second part that extends along the lengthwise direction of the stent, and the second part is open on one side; and
        a third part symmetrically formed to the first part, the third part is a mirror image of the first part around the virtual axis located through the center of the second part, the third part being joined to the second part;
    wherein the second part of the cell comprises a first unit having at least four curved portions, located at a first side of the second part, and a second unit at a second side of the second part, in which the first unit is symmetrically joined to the second unit with respect to the virtual axis through the center of the second part that extends along the lengthwise direction of the stent.

2. An expanding vascular stent comprising:
    a body that is hollow in the lengthwise direction, wherein:
    the body includes a plurality of rows connected to each other via a plurality of links, each row including a plurality of cells joined together; and
    the adjacent rows are located in such a way that the plurality of cells in one row are symmetrically formed to the plurality of cells in another row, in an out of phase array; and
    wherein the links connecting a first row to a second row that is adjacent to the first row are:
        parallel to each other;
        parallel to straight portions on the cells of the first row, parallel to straight portions on cells of the second row, and parallel to straight portions on cells of a third row, the third row being adjacent to the second row; and
        perpendicular to the links connecting the second row to the third row;
    wherein each of the plurality of cells comprises:
        a first part having a plurality of curved portions, the first part being symmetrically formed with respect to a virtual axis that extends along the lengthwise direction of the stent, and open on one side;
        a second part having a plurality of curved portions, wherein the second part is joined to the first part, one end of the second part is symmetrically formed to the other end of the second part with respect to the virtual axis located through a center of the second part that that extends along the lengthwise direction of the stent, and the second part is open on one side; and
        a third part symmetrically formed to the first part, the third part is a mirror image of the first part around the virtual axis located through the center of the second part, the third part being joined to the second part;
    wherein the second part of the cell comprises a first unit having at least four curved portions, located at a first side of the second part, and a second unit at a second side of the second part, in which the first unit is symmetrically joined to the second unit with respect to the virtual axis through the center of the second part that extends along the lengthwise direction of the stent.

3. An expanding vascular stent comprising:
    a body that is hollow in the lengthwise direction, including a plurality of cells joined together,
    wherein each of the plurality of cells includes at least two or more parts whose body is curved numerous times and whose one side is opened, in which both ends of the parts are extended with a curved portion, the curved portions being curved in the same direction; and
    wherein each of the plurality of cells comprises:
        a first part having a plurality of curved portions, the first part being symmetrically formed with respect to a virtual axis that extends along the lengthwise direction of the stent, and open on one side;
        a second part having a plurality of curved portions, wherein the second part is joined to the first part, one end of the second part is symmetrically formed to the other end of the second part with respect to the virtual axis located through a center of the second part that extends along the lengthwise direction of the stent, and the second part is open on one side; and
        a third part symmetrically formed to the first part, the third part is a mirror image of the first part around the virtual axis located through the center of the second part, the third part being joined to the second part;

wherein the body comprises:
  the first row comprised of a plurality of cells joined together;
  the second row comprised of a plurality of cells joined together; and
  a link connecting the second part in the first row to the second part in the second row; and
wherein each second part comprises:
  a first unit having at least four curved portions, located at one side of the second part;
  a second unit that is located at the other side of the second part and symmetrically joined to the first unit with respect to the virtual axis through the center of the second part; and
  the link connects the second unit of the second part in the first row to the first unit of the second part in the second row.

4. An expanding vascular stent comprising:
a body that is hollow in the lengthwise direction, wherein:
the body includes a plurality of rows connected to each other via a plurality of links, each row including a plurality of cells joined together; and
the adjacent rows are located in such a way that the plurality of cells in one row are symmetrically formed to the plurality of cells in another tow, in an out of phase array; and
wherein the links connecting a first row to a second row that is adjacent to the first row are:
  parallel to each other;
  parallel to straight portions on the cells of the first row, parallel to straight portions on cells of the second row, and parallel to straight portions on cells of a third row, the third row being adjacent to the second row; and
  perpendicular to the links connecting the second row to the third row;
wherein each of the plurality of cells comprises:
  a first part having a plurality of curved portions, the first part being symmetrically formed with respect to a virtual axis that extends along the lengthwise direction of the stent, and open on one side;
  a second part having a plurality of curved portions, wherein the second part is joined to the first part, one end of the second part is symmetrically formed to the other end of the second part with respect to the virtual axis located through a center of the second part that that extends along the lengthwise direction of the stent, and the second part is open on one side; and
  a third part symmetrically formed to the first part, the third part is a mirror image of the first part around the virtual axis located through the center of the second part, the third part being joined to the second part;
wherein the body comprises:
  the first row comprised of a plurality of cells joined together;
  the second row comprised of a plurality of cells joined together; and
  a link connecting the second part in the first row to the second part in the second row; and
wherein each second part comprises:
  a first unit having at least four curved portions, located at one side of the second part;
  a second unit that is located at the other side of the second part and symmetrically joined to the first unit with respect to the virtual axis through the center of the second part; and
  the link connects the second unit of the second part in the first row to the first unit of the second part in the second row.

5. An expanding vascular stent comprising:
a body that is hollow in the lengthwise direction,
wherein:
the body includes a plurality of rows connected to each other via a plurality of links, each row including a plurality of cells joined together; and
the adjacent rows are located in such a way that the plurality of cells in one row are symmetrically formed to the plurality of cells in another row, in an out of phase array; and
wherein the links connecting a first row to a second row that is adjacent to the first row are:
  parallel to each other;
  parallel to straight portions on the cells of the first row, parallel to straight portions on cells of the second row, and parallel to straight portions on cells of a third row, the third row being adjacent to the second row; and
  perpendicular to the links connecting the second row to the third row;
wherein the body comprises:
the first row having a plurality of cells joined together;
the second row having a plurality of cells joined together;
the third row having a plurality of cells joined together;
a first link connecting a first part in the first row to a third part in the second row;
a second link connecting a second part in the first row to another second part in the second row; and
the first link and the second link are out of phase.

\* \* \* \* \*